US012414861B2

(12) United States Patent
Ek et al.

(10) Patent No.: US 12,414,861 B2
(45) Date of Patent: *Sep. 16, 2025

(54) MICROFRACTURE APPARATUSES AND METHODS (71) Applicant: ANIKA THERAPEUTICS, INC., Bedford, MA (US)

(72) Inventors: Steven Ek, Durham, NH (US); George Sikora, Bridgewater, MA (US)

(73) Assignee: ANIKA THERAPEUTICS, INC., Bedford, MA (US)

( * ) Notice: Subject to any disclaimer, the term of this patent is extended or adjusted under 35 U.S.C. 154(b) by 233 days.

This patent is subject to a terminal disclaimer.

(21) Appl. No.: 18/136,154

(22) Filed: Apr. 18, 2023

(65) Prior Publication Data
US 2023/0355406 A1 Nov. 9, 2023

Related U.S. Application Data (63) Continuation of application No. 16/946,758, filed on Jul. 6, 2020, now Pat. No. 11,660,207, which is a continuation of application No. 14/863,554, filed on Sep. 24, 2015, now Pat. No. 10,702,395.

(60) Provisional application No. 62/058,190, filed on Oct. 1, 2014.

(51) Int. Cl.
A61F 2/46 (2006.01)
A61B 17/88 (2006.01)

(52) U.S. Cl.
CPC ............ *A61F 2/4601* (2013.01); *A61B 17/88* (2013.01); *A61F 2/46* (2013.01); *A61F 2002/4687* (2013.01)

(58) Field of Classification Search
CPC .. A61F 2/46; A61F 2/4601; A61F 2/08; A61F 2/0805; A61F 2/00; A61F 2/0063; A61F 2/40; A61B 17/88; A61B 17/16; A61B 17/1604; A61B 17/17; A61B 17/1732; A61B 17/1735
See application file for complete search history.

(56) References Cited

U.S. PATENT DOCUMENTS

| | | | | |
|---|---|---|---|---|
| 5,766,246 A * | 6/1998 | Mulhauser | ................ | A61F 2/02 623/23.72 |
| 10,702,395 B2 * | 7/2020 | Ek | ......................... | A61F 2/4601 |
| 11,660,207 B2 * | 5/2023 | Ek | ............................. | A61F 2/46 606/86 R |
| 2004/0267277 A1 * | 12/2004 | Zannis | .................. | A61F 2/4618 606/86 R |
| 2010/0191195 A1 * | 7/2010 | Kirschenbaum | ... | A61B 17/1604 604/272 |

* cited by examiner

*Primary Examiner* — Christopher J Beccia
(74) *Attorney, Agent, or Firm* — GOODWIN PROCTER LLP (57) ABSTRACT

Embodiments of apparatuses and methods for microfracture (e.g., forming a plurality of microfractures in a bone to encourage cartilage regeneration).

19 Claims, 8 Drawing Sheets

MICROFRACTURE APPARATUSES AND METHODS

CROSS-REFERENCE TO RELATED APPLICATIONS

This application is a continuation of U.S. patent application Ser. No. 14/863,554, filed Sep. 24, 2015, now U.S. Pat. No. 10,702,395, issued Jul. 7, 2020, which claims the benefit of priority to U.S. Provisional Patent Application No. 62/058,190, filed Oct. 1, 2014, hereby incorporated by reference in their entirety.

BACKGROUND

1. Field of the Invention

The present invention relates generally to orthopedic treatments, more particularly, but not by way of limitation, to devices and methods for treating and/or creating microfractures (e.g., in subchondral bone).

2. Description of Related Art

Examples of treatment methods and apparatuses for creating microfractures in bone are disclosed in (1) J. P. Benthien, et al., *The treatment of chondral and osteochondral defects of the knee with autologous matrix-induced chondrogenesis (AMIC): method description and recent developments*, Knee Surg Sports Traumatol Arthrose, August 2011, 19(8):1316-1319; (2) Thomas J. Gill, M D, et al., *The Treatment of Articular Cartilage Defects Using the Microfracture Technique*, Journal of Orthopaedic & Sports Physical Therapy, October 2006, 36(10):728-738; (3) L. de Girolamo, *Treatment of chondral defects of the knee with one step matrix-assisted technique enhanced by autologous concentrated bone marrow: In vitro characterisation of mesenchymal stem cells from iliac crest and subchondral bone*, Injury, Int. J. Care Injured 41 (2010) 1172-1177; (4) Pub. No. US 2009/0143782; (5) Pub. No. US 2005/0043738; (6) Pub. No. US 2005/0021067; and (7) Pub. No. US 2004/0147932.

SUMMARY

This disclosure includes embodiments of apparatuses, kits, and methods for treating and/or creating microfractures in bone (e.g., subchondral bone). At least some of the present embodiments are configured to deliver and/or localize active ingredients or biological responses near the microfracture site, such as, for example, growth factor(s), anticoagulant(s), protein(s), medicine(s), and/or the like, using a membrane to enclose, at least partially, the microfracture site.

Some embodiments of the present apparatuses comprise: a guide (e.g., comprising: a platform having a first side, a second side, and a hole extending through the first and second sides, the first side configured to receive a membrane; and a guide tube having a first end, a second end, and a channel extending from the first end to the second end, the first end configured to be coupled to the platform such that the hole of the platform is in fluid communication with the channel of the guide tube); and an applicator comprising a first end, a second end, and an elongated body extending from the first end to the second end, the elongated body having a length greater than a length of the guide tube, the second end of the applicator configured to push a membrane through the guide tube to an application site in a patient. In some embodiments, the first side of the platform includes a recess that is configured to receive a membrane. In some embodiments, the platform and the guide tube are unitary. In some embodiments, the first end of the applicator includes an enlarged handle. In some embodiments, the first end of the applicator is configured to be engaged by a machine. In some embodiments, the second end of the applicator includes a resilient tip. In some embodiments, the second end of the applicator has a rounded shape. In some embodiments, the second end of the applicator has a transverse dimension that is larger than a transverse dimension of the elongated body.

Some embodiments of the present surgical guide apparatuses comprise: a platform having a first side, a second side, and a hole extending through the first and second sides, the first side including a recess that is configured to receive a membrane; and a guide tube having a first end, a second end, and a channel extending from the first end to the second end, the first end configured to be coupled to the platform such that the hole of the platform is in fluid communication with the channel of the guide tube.

Some embodiments of the present apparatuses comprise: a platform for a surgical guide, the platform having a first side, a second side, and a hole extending through the first and second sides, the first side including a recess that is configured to receive a membrane, where the platform is configured to be coupled to a guide tube. In some embodiments, the first side of the platform has a maximum transverse dimension that is at least twice as large as a maximum thickness of the platform. In some embodiments, the platform has an elongated shape with rounded ends. In some embodiments, the recess is rectangular. In some embodiments, the recess has a maximum depth of 5 millimeter (mm). In some embodiments, the first end of the guide tube has a first outer transverse dimension and the second end of the guide tube has a second outer transverse dimension that is smaller than the first transverse dimension. In some embodiments, the channel has an inner maximum transverse dimension of 10 millimeters (mm) at a point located nearer the second end of the guide tube than the first end.

Some embodiments of the present kits comprise: an embodiment of the present platforms having a recess configured to receive a membrane; a membrane disposed in the recess of the platform; a package within which the platform and membrane are disposed; and where the platform and membrane are sterile.

Some embodiments of the present kits comprise: an embodiment of the present apparatuses in which the first side of the platform includes a recess configured to receive a membrane; a membrane disposed in the recess of the platform; a package within which the apparatus and membrane are disposed; where the apparatus is sterile.

Some embodiments of the present methods comprise: pushing a membrane through a guide tube to cover a microfracture in an articular surface of a patient with the membrane, where the guide tube extends through the patient's skin such that a distal end of the guide tube is adjacent the microfracture as the membrane exits the guide tube. Some embodiments further comprise: providing a platform with a first side, a second side, a hole extending through the first and second sides, where the first side includes a recess that is configured to receive a membrane, and the membrane is disposed in the recess; and coupling the platform to a guide tube prior to pushing the membrane through the guide tube. In some embodiments, the membrane is at least partially folded as it enters the guide tube and at least partially returns to its pre-folded form at the end of the applicator as the applicator pushes the membrane past the first end of the guide tube.

Any embodiment of any of the present apparatuses and methods can consist of or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

Details associated with the embodiments described above and others are presented below.

BRIEF DESCRIPTION OF THE DRAWINGS

The following drawings illustrate by way of example and not limitation. For the sake of brevity and clarity, every feature of a given structure is not always labeled in every figure in which that structure appears. Identical reference numbers do not necessarily indicate an identical structure. Rather, the same reference number may be used to indicate a similar feature or a feature with similar functionality, as may non-identical reference numbers. The figures are drawn to scale (unless otherwise noted), meaning the sizes of the depicted elements are accurate relative to each other for at least the embodiment depicted in the figures.

FIG. 1I) depicts a cross-sectional view of a first end of the cannula shown in FIG. 1A.

DESCRIPTION OF ILLUSTRATIVE EMBODIMENTS

The term "coupled" is defined as connected, although not necessarily directly, and not necessarily mechanically; two items that are "coupled" may be unitary with each other. The terms "a" and "an" are defined as one or more unless this disclosure explicitly requires otherwise. The term "substantially" is defined as largely but not necessarily wholly what is specified (and includes what is specified; e.g., substantially 90 degrees includes 90 degrees and substantially parallel includes parallel), as understood by a person of ordinary skill in the art. In any embodiment of the present apparatuses, kits, and methods, the term "substantially" may be substituted with "within [a percentage] of" what is specified, where the percentage includes 0.1, 1, 5, and/or 10 percent.

The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, an apparatus or kit that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Further, an apparatus, device or system that is configured in a certain way is configured in at least that way, but it can also be configured in other ways than those specifically described.

Referring now to the drawings, and more particularly to FIGS. 1A-2C, shown therein and designed by the reference numeral 10 is one embodiment of an apparatus for creating microfractures in bone (e.g., subchondral bone). In the embodiment shown, apparatus 10 comprises a penetrator 14, a cannula 18, and a handle 22 coupled to cannula 18. In other embodiments (e.g., as shown in FIG. 3), handle 22 may be omitted. In the embodiment shown, cannula 18 has a first end 26, a second end 30, and a channel 34 extending between the first end and the second end. Such first and second ends should be understood as the locations of the beginning and end of the channel. In this embodiment, cannula 18 has a primary portion 38 and a distal portion 42, with primary portion 38 extending between first end 26 and distal portion 42 (e.g., a majority of the length of the cannula, as in the embodiment shown), and with distal portion 42 extending between primary portion 38 and second end 30. The distal portion can be configured such that a second end of the channel (at second end 30) is disposed at an angle relative to a first end of the channel (at first end 26). For example, in the embodiment shown, distal portion 42 is disposed at an angle 46 relative to the primary portion. In the embodiment shown, angle 46 is between 10 and 30 degrees (e.g., 20 degrees). In other embodiments, angle 46 can be any size that permits apparatus 10 to function as described in this disclosure (e.g., angle 46 can be equal to, or between any two of: 0, 10, 20, 30, 40, 45, 50, and/or 60 degrees). In other embodiments, angle 46 can be greater than 60 degrees (e.g., equal to, or between any two of: 60, 70, 80, 90, and/or more degrees). As a further example, distal portion 42 can include a curved or hooked shape such that angle 46 is effectively larger than 90 degrees (e.g., equal to, or between any two of: 90, 120, 150, 180, and/or 180 degrees).

Figure 1A:
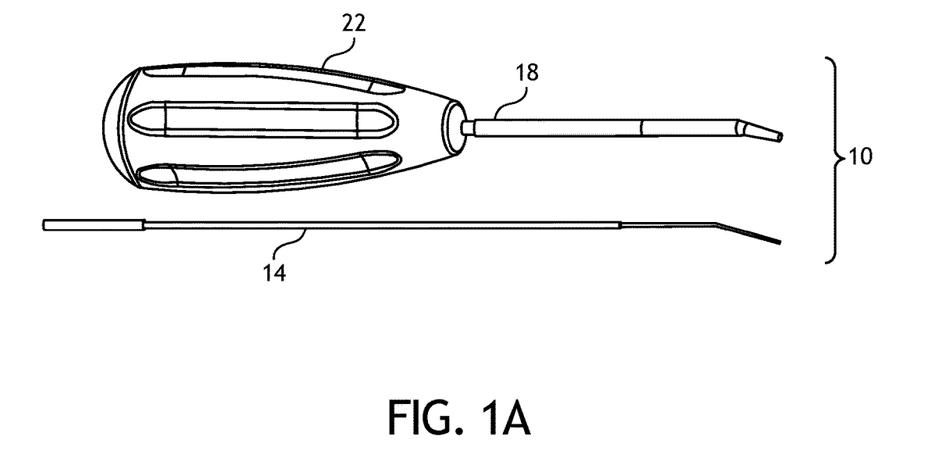
FIG. 1A depicts a perspective view of an apparatus for creating subchondral bone microfractures having a cannula and a penetrator.
Figure 1B:
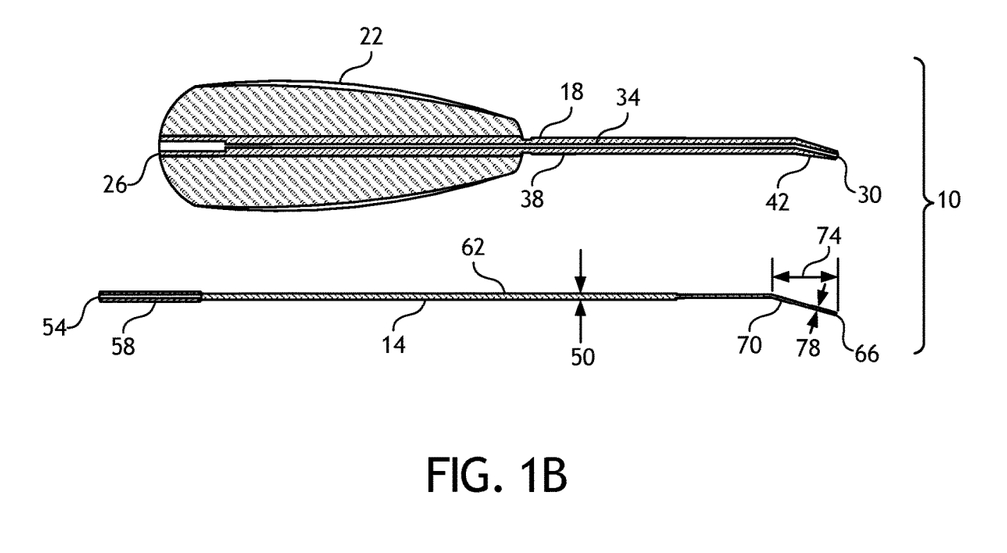
FIG. 1B depicts a cross-sectional view of the apparatus of FIG. 1A.

Primary portion 38 has a transverse dimension 50 (e.g., a diameter, in the embodiment shown). Penetrator 14 and cannula 18 can comprise any suitable material that permits the apparatus to function as described in this disclosure (e.g., and permits the penetrator and the cannula to be sterilized). For example, in some embodiments, penetrator 14 comprises nickel-titanium alloy (e.g., Nitinol), and/or cannula 18 comprises metal, such as stainless steel (e.g., a surgical stainless steel). Embodiments of the present cannulas are rigid and configured not to flex or bend during use. In other embodiments, penetrator 14 can comprise a biocompatible metal such as stainless steel (e.g., 316L stainless steel).

Figure 1C:
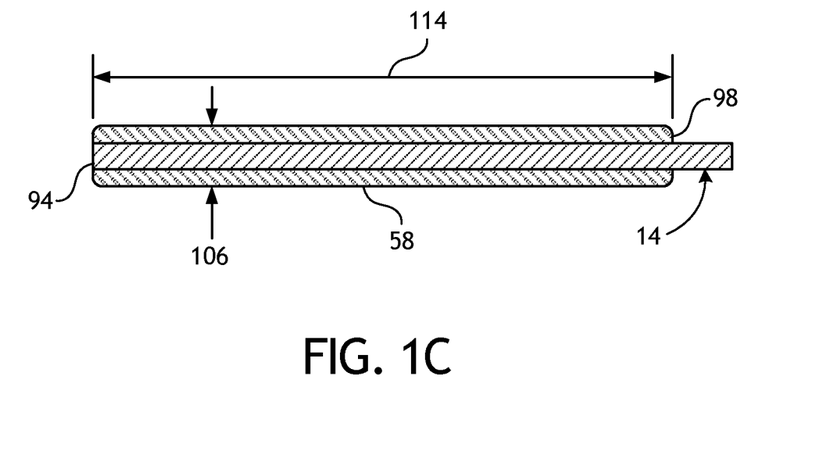
FIG. 1C depicts a cross-sectional view of an enlarged head of the penetrator shown in FIG. 1A.

In the embodiment shown, penetrator 14 has a proximal end 54, an enlarged head 58 adjacent proximal end 54, a primary portion 62, a distal end 66 (e.g., pointed distal end 66, as shown), and a penetration portion 70 adjacent distal end 66. In this embodiment, penetration portion 70 has a length 74 that is a minority of the length of penetrator 14 between proximal end 54 and distal end 66. In some embodiments, penetrator 14 has a transverse dimension of less than 1.2 mm (e.g., between 1 mm and 1.1 mm; less than 1.1 mm, less than 1.05 mm, less than 1 mm; less than, or between any two of, 0.5, 0.6, 0.7, 0.8, 0.9, and/or 1 mm). For example, in the embodiment shown, penetration portion 70 has a circular cross-section with a diameter 78 of between 0.7 and 0.8 mm (e.g., 0.78 mm). In some embodiments, penetration portion 70 has a circular cross-section with a diameter of between 1 and 1.1 mm (e.g., 1.04 mm). Penetrator 14 is configured to be disposed in channel 34 of cannula 18 such that penetrator 14 is movable between a (1) retracted position (e.g., in which distal end 66 of the penetrator does not extend beyond second end 30 of the cannula) and (2) an extended position in which distal end 66 of the penetrator extends beyond second end 30 of the cannula by a penetration distance 82. In some embodiments, penetration distance 82 is at least (e.g., greater than) 5 mm (e.g., 7 mm, 8 mm, 8-10 mm, more than 10 mm) and/or at least (e.g., greater than) 5 times (e.g., greater than, or between any two of: 6, 7, 8, 9, 10, or more times) a transverse dimension (e.g., diameter) of penetrator 14 (e.g., diameter 78 of penetration portion 70). For example, in the embodiment shown, penetration distance 82 is between 8 mm and 10 mm (e.g., 10 mm), which is greater than 12 times diameter 78. In the embodiment shown, diameter 50 of primary portion 38 is larger than diameter 78 of penetration portion 70. In some embodiments, diameter 50 is also less than 1.2 mm (e.g., between 1 mm and 1.1 mm, less than 1.1 mm, less than 1.05 mm). In some embodiments, diameter 50 is substantially equal to diameter 78. In some embodiments, penetrator 14 comprises a central wire defining diameter 78 that is encircled or encased by an outer tubing (e.g., metallic tubing, plastic shrink wrap, and/or the like along the length of primary portion 62 to define transverse dimension 50.

In some embodiments, a coating is disposed on at least penetration portion 70 of penetrator 14 (the coating may also be disposed on primary portion 62 of the penetrator). In some embodiments, the coating is hydrophilic. Examples of hydrophilic coatings include Hydro-Silk coatings available from TUA Systems of Florida (U.S.A.). In some embodiments, the coating comprises silver ions. In some embodiments, the coating comprises one or more active ingredients configured to elicit or stimulate a biological response in (e.g., bone or cartilage) tissue, such as, for example, growth factor(s), anticoagulant(s), protein(s), and/or the like. Such coatings can be applied as known in the art for the materials used in particular embodiments.

In the embodiment shown, cannula 18 is configured to provide lateral support for penetrator 14, such as to prevent the penetrator from bending or buckling while being driven into the hard subchondral bone. For example, in the embodiment shown, diameter 50 of primary portion 62 of the penetrator is nearly as large as (e.g., greater than, or between any two of: 95, 96, 97, 98, 99, and or 100 percent of) the diameter of channel 34, and diameter 78 of penetration portion 70 is greater than 75% (e.g., greater than, or between any two of: 75, 80, 85, 90, 95, and/or 100 percent of) the diameter of channel 34 (e.g., the diameter of channel 34 adjacent second end 30 of the cannula). In some embodiments, penetrator 14 is substantially straight prior to being disposed in channel 34 of cannula 18, such that inserting the penetrator into the cannula causes the penetration portion 70 of the penetrator to be angled relative to primary portion 62. In some such embodiments, penetrator 14 may be resilient enough to (e.g., at least partially) return to its straight shape after removal from the cannula.

In some embodiments, penetrator 14 is configured to be moved or advanced (e.g., substantially without rotation of the penetrator) from the retracted position to the extended position (FIG. 2B) to form a microfracture in subchondral bone (e.g., in a patient's knee or shoulder joint), the microfracture having a depth of at least (e.g., more than) 5 mm (e.g., 7 mm, 8 mm, 8-10 mm, more than 10 mm) and/or at least (e.g., greater than) 5 times (e.g., greater than, or between any two of: 6, 7, 8, 9, 10, or more times) a transverse dimension (e.g., diameter) of penetrator 14 (e.g., diameter 78 of penetration portion 70). For example, in the embodiment shown, penetrator 14 is configured to be moved or advanced (e.g., substantially without rotation of the penetrator, which includes no rotation up to rotation of less than one full revolution clockwise and/or counterclockwise from the position at which distal end 66 of the penetrator first contacts the bone) from the retracted position to the extended position (FIG. 2B) to form a microfracture in subchondral bone (e.g., in a patient's knee or shoulder joint), the microfracture having a depth of between 8 mm and 10 mm (e.g., 10 mm), which is greater than 12 times diameter 78. In the embodiment shown, penetrator 14 is configured to be moved or advanced manually to the extended position. As used in this disclosure, moved or advanced "manually" means without the assistance of an external energy source other than that provided by a user. For example, if the penetrator is moved or advanced with a battery-powered or spring-driven driver, it would not be "manually." Conversely, the penetrator would be moved or advanced "manually" if a mallet, hammer, or other tool is swung by a user (e.g., in the user's hand) to impact first end 26 of the penetrator. In some embodiments, the present apparatuses are configured such that the penetrator can (but need not) be rotated as it is advanced or moved from the retracted position to the advanced position. For example, a portion of the penetrator (e.g., enlarged head 58) can be disposed in the chuck of a drill such that the drill can rotate the penetrator. In such embodiments, the penetrator may (hut need not) be substantially straight or axial (without bends) along its entire length (e.g., prior to being disposed in a cannula with an angled distal portion).

Figure 1D:
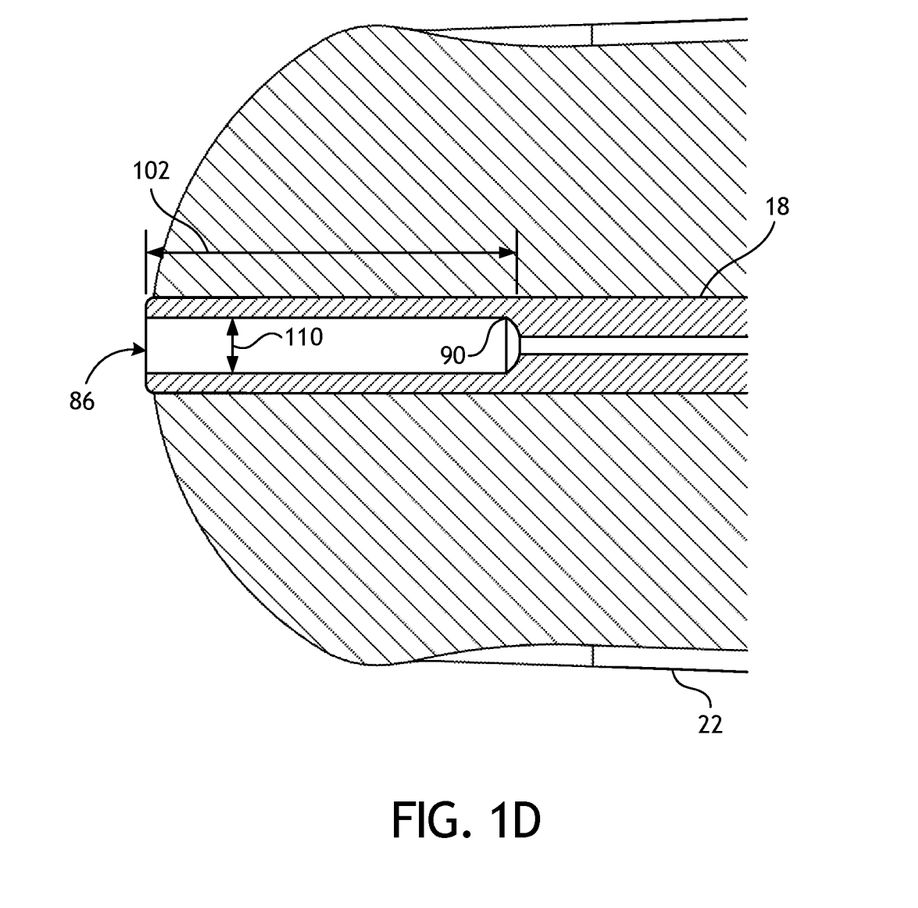
Figure 2A:
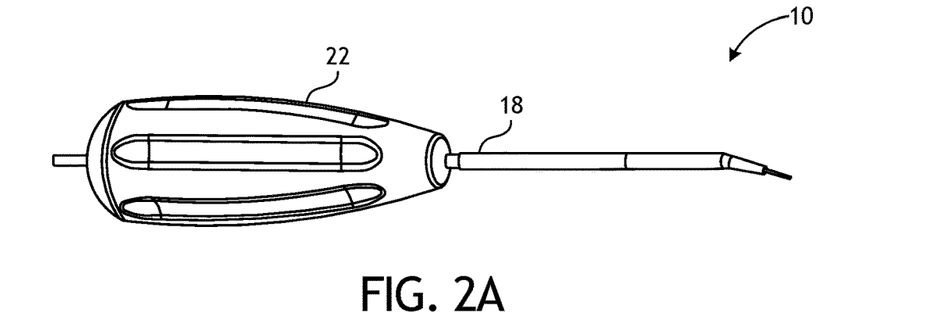
FIG. 2A depicts a perspective view of the apparatus of FIG. 1A, with the penetrator shown in the cannula.
Figure 2B:
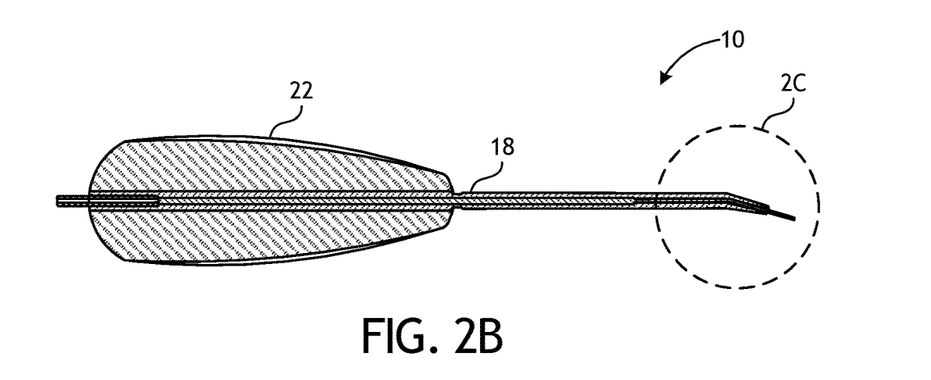
FIG. 2B depicts a cross-sectional view of the apparatus of FIG. 1A, with the penetrator shown in the cannula.
Figure 2C:
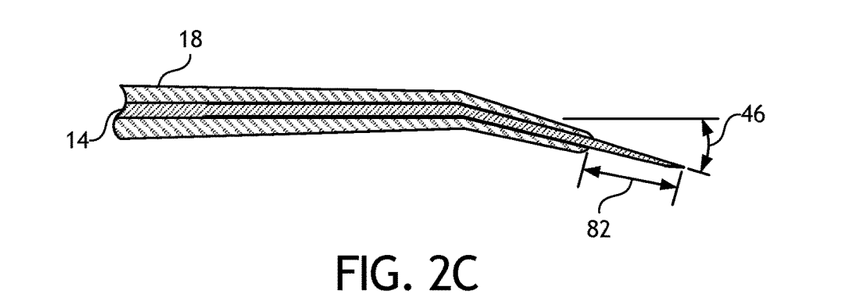
FIG. 2C depicts a cross-sectional view of a portion of the apparatus of FIG. 1A that includes a second end of the cannula and a distal end of the penetrator, with the penetrator shown in the cannula.
Figure 3:
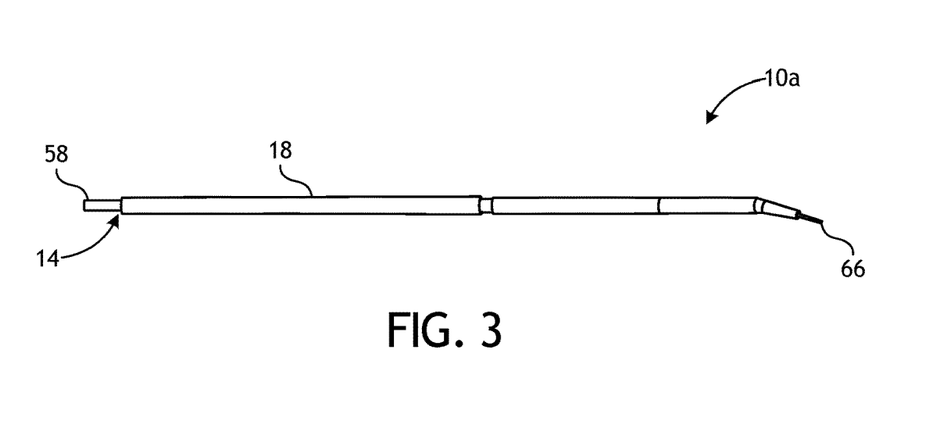
FIG. 3 depicts a perspective view of a second embodiment of an apparatus for creating subchondral bone microfractures.

In the embodiment shown, penetration distance 82 (and the depth of the microfracture the apparatus is configured to create) is limited by enlarged head 58 contacting the cannula (e.g., penetration distance is maximized when enlarged head 58 contacts the cannula, as shown in FIG. 2B). For example, in the embodiment shown, cannula 18 includes a recessed portion 86 and a shelf 90. As shown, recessed portion 86 extends from first end 26 toward second end 30 (inwardly), and shelf 90 is disposed between recessed portion 86 and second end 30 such that penetration distance 82 is limited by enlarged head 58 contacting shelf 90. For example, in the embodiment shown, enlarged head 58 has a cylindrical (e.g., circular cylindrical, as shown) with a first end 94 and a second end 98, and is configured such that second end 98 contacts shelf 90 when the penetrator is in the extended position relative to the cannula (FIG. 2B). In some embodiments, recessed portion 86 can be configured to maintain the orientation or alignment of enlarged head 58 as the penetrator is moved or advanced from the retracted position to the extended position. For example, in some embodiments, recessed portion 58 has a depth 102 that is at least as large as (e.g., is greater than, or between any two of: 100, 110, 120, 130, 140, 150, or more percent of) penetration distance 82 (e.g., such that enlarged head 58 is at least partially within recessed portion 86 when distal end 66 extends beyond second end 30 of the cannula), and/or enlarged head 58 has a transverse dimension (e.g., diameter) that is at least 90% (e.g., greater than, or between any two of: 90, 92, 94, 96, 98, and/or 100 percent) of a corresponding transverse dimension of recessed portion 86 (e.g., such that cannula 18 limits tilting of enlarged head 58 relative to cannula 14, and/or limits misalignment of enlarged head 58 relative to primary portion 62 of the penetrator).

For example, in the embodiment shown, depth 102 of recessed portion 58 is between 175% and 250% (e.g., between 200% and 225%) of penetration distance 82. In this embodiment, enlarged head 58 and recessed portion 86 each has a circular cross section, and enlarged head 58 has a diameter 106 that is between 90% and 100% (e.g., between 95% and 100%) of diameter 110 of recessed portion 86. In some embodiments, a length 114 of enlarged head 58 is at least 150% (e.g., at least, or between any two of: 150, 175, 200, 225, 250, 300, or more percent) of penetration distance 82. For example, in the embodiment shown, length 114 is over 300% of penetration distance 82, such that a portion of enlarged head 58 that is at least as long as penetration distance 82 is disposed in recessed portion 86 when distal end 66 of the penetrator is even with second end 30 of the cannula (and the orientation of enlarged head 58 relative to cannula 18 is thereby maintained). In some embodiments, enlarged head 58 has an elongated shape such that length 114 is greater than (e.g., greater than, or between any two of: 2, 3, 4, 6, 8, or more times) diameter 106. For example, in the embodiment shown, length 114 is between 8 and 12 times diameter 106.

FIG. 3 depicts a second embodiment 10a of a microfracture apparatus. Apparatus 10a is substantially similar to apparatus 10, with the exception that apparatus 10a does not include a handle (e.g., handle 22).

Embodiments of microfracture device kits can comprise one or more of the present cannulas (e.g., cannula 14) and a reusable tray or other container in a package (e.g., a sealed pouch or the like), where both the cannula(s) and the tray are or can be sterilized (and can be re-sterilized in advance of being re-used). Both the tray and the package may be rectangular in shape. In addition, some embodiments of microfracture device kits can also include two or more penetrators configured to create different microfractures. For example, some embodiments of the microfracture device kits comprise one or more of the present cannulas, a sterilizable tray, a first penetrator configured to have a penetration distance of between 5 mm and 8 mm when used in combination with the cannula, and a second penetrator configured to have a penetration distance greater than 8 mm when used in combination with the cannula. More specifically, some embodiments of the microfracture device kits may include a package (e.g., a box or a flexible package) that comprises sterilized versions of these items. Other embodiments of the microfracture device kits comprise one or more of the present penetrators (e.g., a single penetrator or two penetrators having different penetration depths, different tip diameters, different tip shapes, and/or the like) that are sterile and disposed in a package. Embodiments of the microfracture device kits may also include, in more specific embodiments, instructions for use, which instructions may be inside the package (e.g., as an insert) or outside the package (such as a sticker on the package).

Figure 4A:
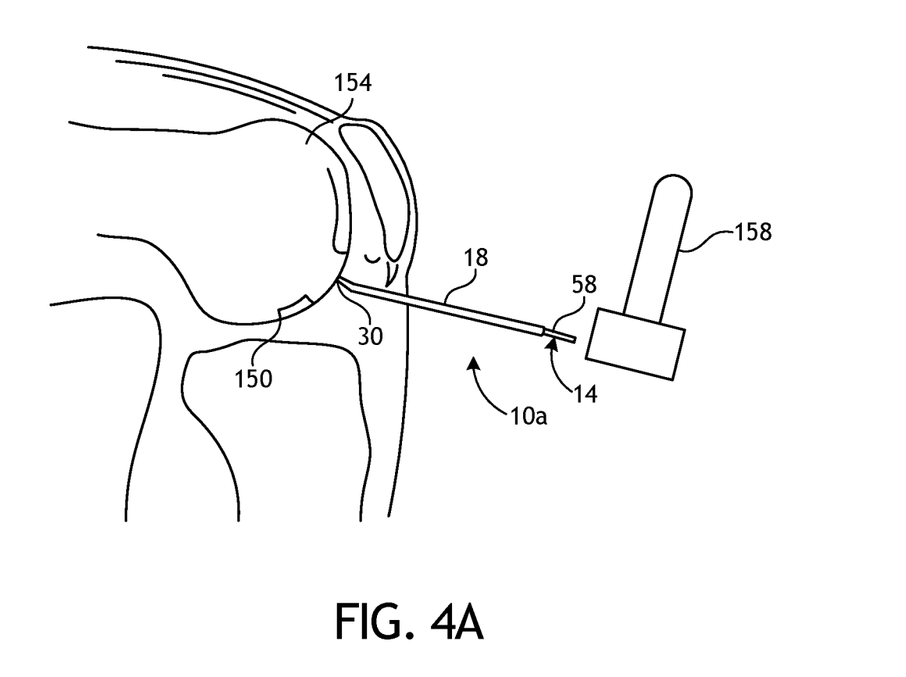
FIGS. 4A and 4B depict perspective views of the apparatus of FIG. 3 positioned for use relative to a patient's knee, and are not drawn to scale.
Figure 4B:
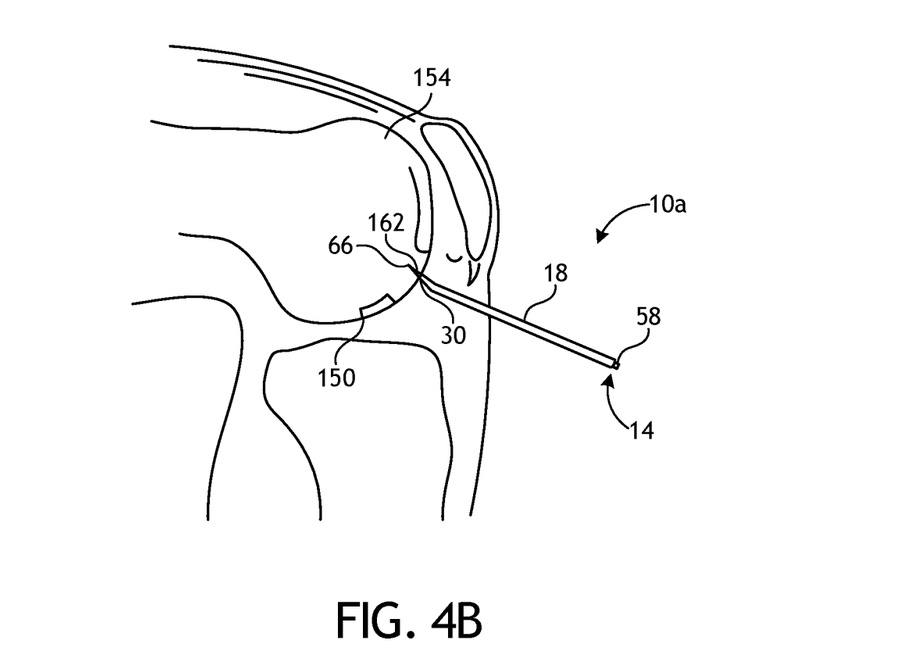

FIGS. 4A and 4B depict an example of microfracture methods (e.g., using embodiment 10a of the microfracture apparatuses). Some embodiments of these methods comprise: disposing an embodiment of the present microfracture apparatuses (e.g., 10, 10a) adjacent to subchondral bone of a patient (e.g., in the knee, shoulder, or other joint). For example, in the embodiment shown, apparatus 10a is disposed adjacent to subchondral bone of articular surface 150 in a patient's knee 154 (e.g., with second end 30 of cannula 18 in contact with the subchondral bone, as shown). Some embodiments further comprise moving or advancing penetrator 14 relative to cannula 18 (e.g., from FIG. 4A to FIG. 4B) until distal end 66 of the penetrator extends into the subchondral bone (as in FIG. 4B) to form a microfracture having a depth of at least 5 mm. For example, in the embodiment shown, penetrator 18 is manually advanced substantially without rotation of the penetrator by striking or impacting proximal end 54 of the penetrator with a mallet 158 until distal end 66 extends into the subchondral bone by a distance of, and forms a microfracture 162 having a depth of, 10 mm. In the embodiment shown, the position of second end 30 of the cannula relative to the subchondral bone remains substantially constant while advancing the penetrator into the bone. In some embodiments of the microfracture methods, the apparatus is repeatedly disposed adjacent the bone (e.g., with second end 30 of the cannula in contact with the subchondral bone and/or in contact with cartilage, such as, for example, cartilage around the perimeter of a lesion), and the penetrator is repeatedly advanced into the subchondral bone to form a plurality of microfractures (e.g., having substantially the same depths). In some embodiments, the microfracture methods can be performed on and/or in the surfaces of other joints, such as, for example, the shoulder, the ankle, the hip, and/or the patellofemoral joint within the knee.

Figures 5A, 5B:
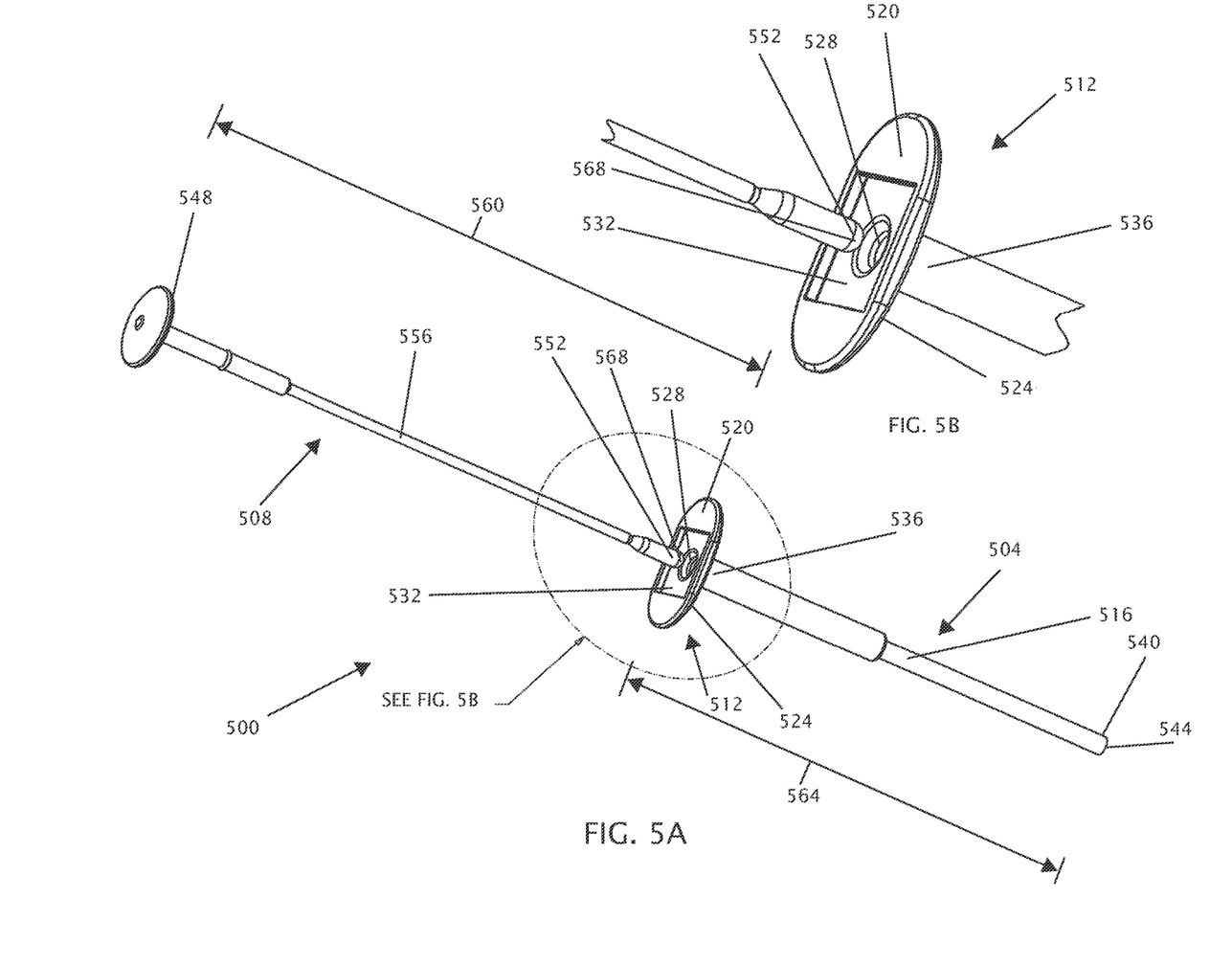
FIG. 5A depicts a perspective view of a first embodiment of the present apparatus for applying a membrane to an articular surface.
FIG. 5B depicts an enlarged perspective view of a portion of the apparatus of FIG. 5A.

FIGS. 5A and 5B depict an embodiment 500 of the present apparatus for treating subchondral bone surfaces (e.g., microfractures in an articular surface of bone). In the embodiment shown, apparatus 500 comprises a guide 504 and an applicator 508. In this embodiment, guide 504 comprises a platform 512 and a guide tube 516. As shown, platform 512 has a first side 520, a second side 524, and a hole 528 extending through the first and second sides. In the depicted embodiment, first side 520 of platform 512 includes a recess 532 that is configured to receive a membrane (e.g., 600 in FIG. 6A-6C). In this embodiment, guide tube 516 has a first end 536, a second end 540, and a channel 544 extending from the first end to the second end. As shown, first end 536 of the guide tube is configured to be coupled to platform 512 such that hole 528 of the platform is in fluid communication with channel 544 of the guide tube. In the embodiment shown, applicator 508 has a first end 548, a second end 552, and an elongated body 556 extending from the first end to the second end. As shown, body 556 has a length 560 (between first and second ends 548, 552) that is greater than a length 564 of the guide tube (between first and second ends 536, 540), and second end 552 of the applicator is configured to push a membrane (e.g., 600) through the guide tube to an application site (e.g., 604) in a patient.

In the embodiment shown, guide tube 516 is unitary with platform 512. In other embodiments, the guide tube (e.g., 516) and the platform (e.g., 512) are not unitary, such that, for example, a user can replace the platform (e.g., if different platforms are needed in a given procedure, such as, for example, for different types of membranes). In some embodiments, the platform (e.g., 512) is preloaded with a membrane (e.g., in a sterile kit or by an assistant aiding a physician in a microfracture procedure), and/or coupled to the guide tube (e.g., 516) while the membrane is disposed in the recess of the platform. Such preloaded embodiments can simplify the use of membranes, which may be difficult to handle during surgery, and/or may reduce the risk of infection by limiting handling of the membrane before it is placed in a patient.

In the embodiment shown, first end 548 of the applicator includes an enlarged handle to assist with manipulation of the applicator. In other embodiments, the first end of the applicator can be configured to be engaged by a machine. In the embodiment shown, second end 552 of the applicator has a transverse dimension that is larger than a transverse dimension of elongated body 556. As shown, second end of the applicator can have a rounded shape. In this embodiment, second end 552 of the applicator comprises a resilient tip 568. Resilient tip 568 can comprise plastic, polymer, latex, rubber, cotton, gauze, textiles and/or the like.

In the embodiment shown, first side 520 of the platform has a maximum transverse dimension that is at least twice as large as a maximum thickness of the platform. As shown, the platform can be an elongated shape with rounded ends. In some embodiments, the platform geometry can be varied based on ergonomic considerations; membrane shape, size, and/or type; manufacturing costs; and/or other considerations, such as for a particular implementation or use. In the embodiment shown, recess 532 is rectangular and has a maximum depth of 5 millimeters (mm). In other embodiments, recess 532 can comprise any shape that is suitable to receive a membrane for a microfracture site (e.g., square, circular, oval, triangular, and/or the like). For example, in some embodiments, certain microfracture sites may be more-readily accessed and/or treated with a membrane that has a circular shape.

In the embodiment shown, channel 544 has an inner maximum transverse dimension of 10 mm at a point located nearer second end 540 of the guide tube than first end 536. In this embodiment, first end 536 of guide tube 516 has a first outer transverse dimension and second end 540 of the guide tube has a second outer transverse dimension that is smaller than the first transverse dimension. In the embodiment shown, for example, adjacent second end 540, the guide tube has an outer diameter of 0.234 inch, and an inner diameter of 0.210 inch, which dimensions may differ in other embodiments (e.g., 0.234±0.05 inches, and 0.210 0.05 inches). In some embodiments, the guide tube has a variable profile. For example, in the embodiment shown, the guide tube has a first section with a substantially uniform outer transverse dimension (e.g., diameter, as shown) along a majority of the length of the guide tube 516, and a second section having a larger and substantially constant outer transverse dimension (e.g., diameter, as shown). In other embodiments, the guide tube can have an outer transverse dimension that tapers along at least a portion of the length of the guide tube.

In the embodiment shown, apparatus 500 is configured to enable controlled and precise placement of membrane 600 at a surgical site. For example, placement of a membrane over a microfracture site can facilitate localization of the biological response created by the microfractures in tissue (e.g., bone or cartilage), such as, for example, generation of growth factor(s), anticoagulant(s), protein(s), and/or the like. In some embodiments of the present apparatus, methods and kits, the membrane can comprise an amniotic membrane such as the PalinGen Flow or PalinGen Membrane available from Amnio Technology LLC. Other human-derived membranes (e.g., human dermal grafts), animal-derived membranes (e.g., animal dermal grafts, and/or therapeutic synthetic membranes can also be used. In other embodiments, the membrane can comprise other materials (e.g., that localize certain biological materials around the microfracture site while allowing other biological materials to leave the microfracture site). The membrane itself may be coated with medication(s), growth factor(s), anticoagulant(s), protein(s), and/or the like.

Figure 6A:
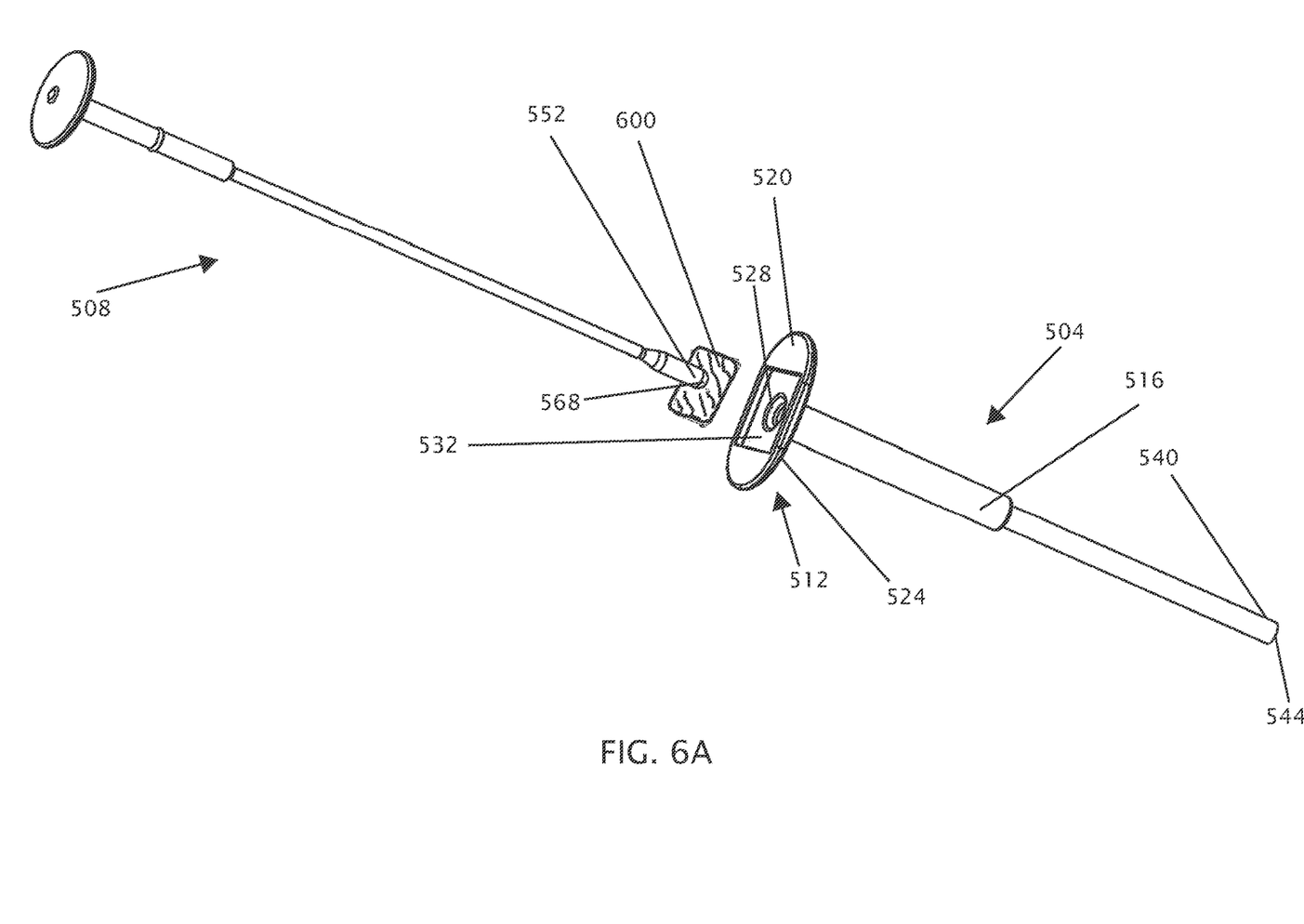
FIG. 6A depicts a perspective view of the apparatus of FIG. 5A shown with a membrane.
Figure 6B:
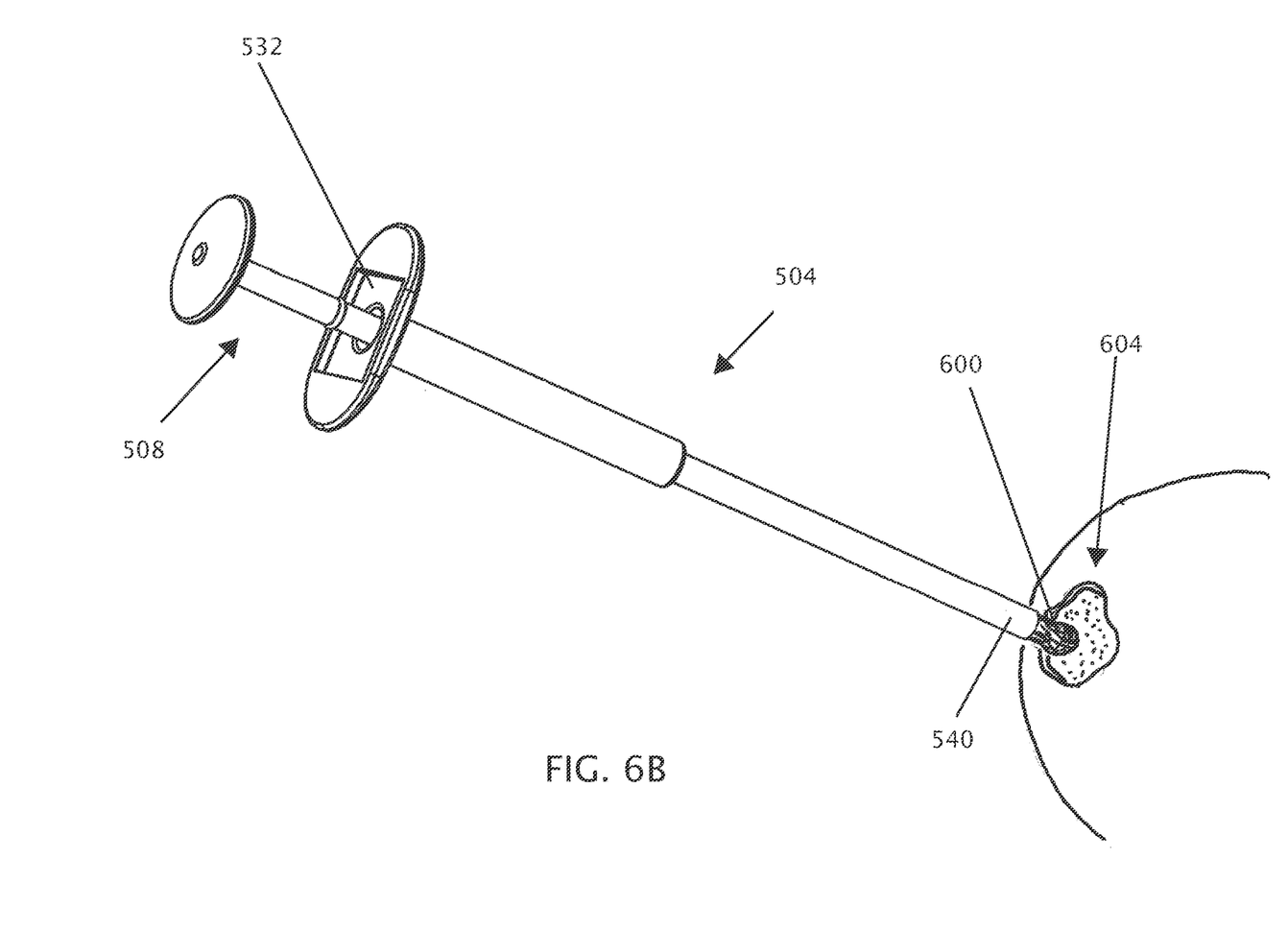
FIG. 6B depicts a perspective view of the apparatus of FIG. 5A shown with a membrane having been guided through a guide tube by an applicator.
Figure 6C:
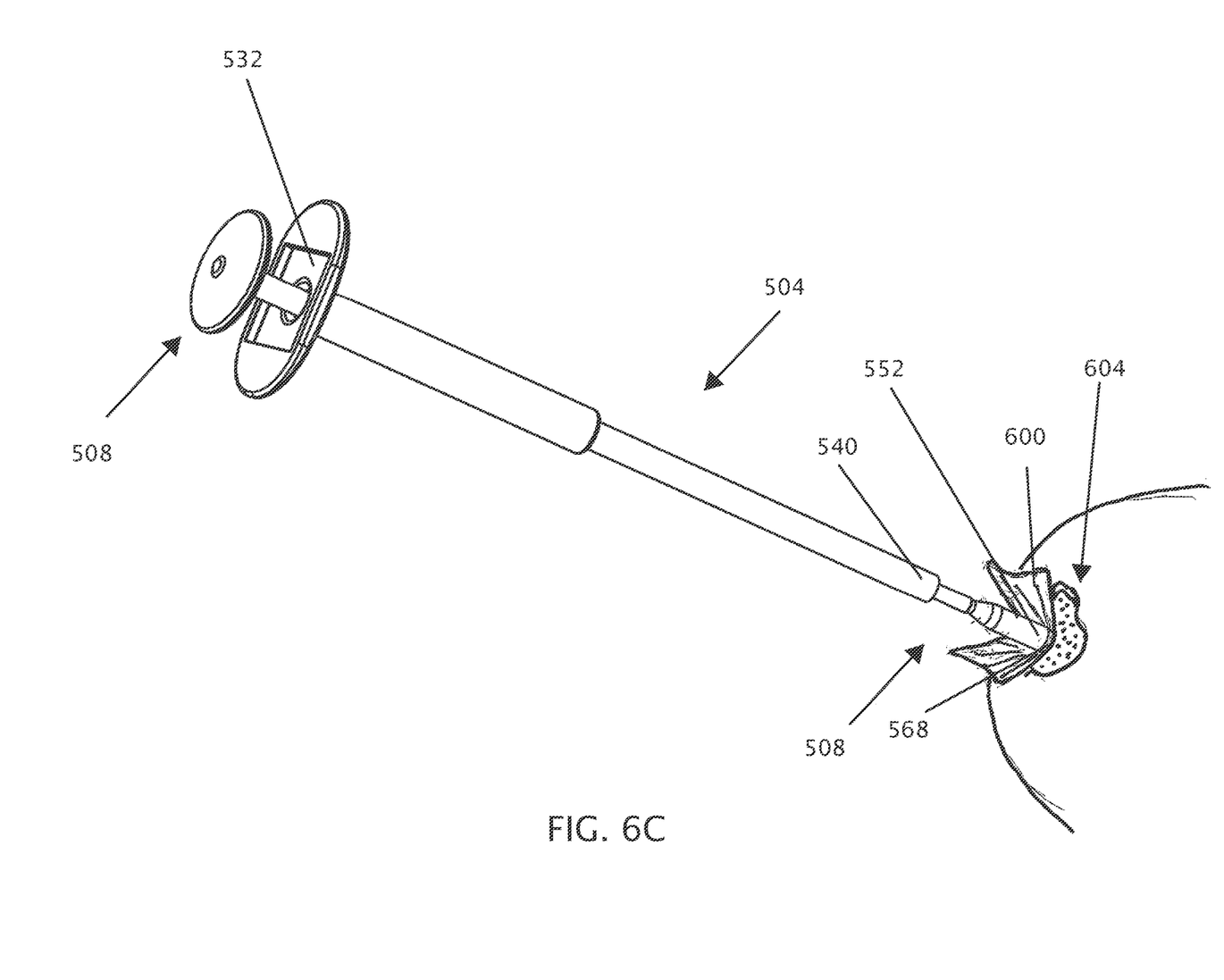
FIG. 6C depicts a perspective view of the apparatus of FIG. 5A with a membrane expanding for application to a microfracture site after passing through the guide tube.

Some embodiments of the present methods comprise: pushing a membrane (e.g., 600) through a guide tube (e.g., 516) to cover a microfracture in an articular surface of a patient with the membrane. In at least some of the present methods, the guide tube can extend through the patient's skin such that a distal end of the guide tube is adjacent the microfracture as the membrane exits the guide tube. FIGS. 6A-6C, for example, illustrate an example of the present method of placing a membrane at a subchondral bone microfracture site 604 in a patient using apparatus 500. In FIG. 6A, membrane 600 is shown between second or distal end 552 of applicator 508 and recess 532 of platform 512. While shown external to recess 532 for illustration purposes, in at least some embodiments, membrane 600 will be positioned in recess 532 for stability and positioning prior to being contacted by applicator 508. End 552 of applicator 508 can then be inserted through hole 528 to collapse and/or fold (as membrane 600 wraps around end 552) and push membrane 600 into and through channel 544.

FIG. 6B shows end 552 of applicator 508 exiting channel 544 of guide tube 516, such that membrane 600 is partially beyond second end 540 but still held in the collapsed or folded state by guide tube 516. As the membrane exits the end of the guide tube, the membrane can at least partially return to its pre-folded or pre-collapsed form. Collapsing or folding the membrane for delivery through a guide tube allows for delivery of the membrane to the application site (e.g., 604) through a relatively smaller incision than would be required without guide tube, and/or without exposing the membrane to fluids around the surgical site.

In some embodiments, the present methods further comprise providing a platform (e.g., 512) with a membrane disposed in a recess (e.g., 532) of the platform; and coupling the platform to a guide tube (e.g., 516) prior to pushing the membrane through the guide tube.

Some embodiments of the present kits comprise: a platform (e.g., 520) for a surgical guide and that is configured to be coupled to a guide tube. Some embodiments further comprise, a membrane disposed in a recess of the platform; and a package within which the platform and membrane are disposed; where the platform and membrane are sterile.

Some embodiments of the present kits comprise: an embodiment of the present apparatuses (e.g., 500). Some embodiments further comprise a membrane disposed in the recess of the platform. Some embodiments further comprise a package within which the apparatus is disposed where the apparatus is sterile.

The above specification and examples provide a complete description of the structure and use of exemplary embodiments. Although certain embodiments have been described above with a certain degree of particularity, or with reference to one or more individual embodiments, those skilled in the art could make numerous alterations to the disclosed embodiments without departing from the scope of this invention. As such, the various illustrative embodiments of the present devices are not intended to be limited to the particular forms disclosed. Rather, they include all modifications and alternatives falling within the scope of the claims, and embodiments other than the one shown may include some or all of the features of the depicted embodiment. For example, penetrator 18 and/or channel 34 can have any suitable cross-sectional shape (e.g., triangular, square, rectangular, and/or the like) that permits the present apparatuses and methods to function as described in this disclosure. For example, components may be combined as a unitary structure, and/or connections may be substituted. Further, where appropriate, aspects of any of the examples described above may be combined with aspects of any of the other examples described to form further examples having comparable or different properties and addressing the same or different problems. Similarly, it will be understood that the benefits and advantages described above may relate to one embodiment or may relate to several embodiments.

The claims are not intended to include, and should not be interpreted to include, means-plus- or step-plus-function limitations, unless such a limitation is explicitly recited in a given claim using the phrase(s) "means for" or "step for," respectively.

What is claimed is:

1. A method for placing a membrane on a surgical site, the steps of the method comprising:
   disposing the membrane in a recess of a platform;
   coupling the platform to a tube;
   collapsing the membrane from a pre-collapsed form to a collapsed form;
   pushing the membrane in the collapsed form through a lumen of the tube to the surgical site, via a distal end of an applicator; and
   transitioning the membrane from the collapsed form to the pre-collapsed form, so as to cover at least a portion of the surgical site.

2. The method of claim 1, further comprising at least partially folding the membrane.

3. The method of claim 2, wherein folding the membrane comprises wrapping the membrane around the distal end of the applicator.

4. The method of claim 1, wherein the surgical site is a microfracture site.

5. The method of claim 1, wherein the step of coupling the platform to the tube is preformed prior to the step of pushing the membrane through the lumen of the tube.

6. The method of claim 1, wherein the recess has a maximum depth of 5 millimeters (mm).

7. The method of claim 1, wherein the recess has a substantially rectangular shape.

8. The method of claim 1, wherein the recess has a shape selected from a group consisting of square, circular, oval, and triangular.

9. The method of claim 1, wherein the platform further comprises an aperture extending therethrough.

10. The method of claim 9, wherein the aperture of the platform is in fluid communication with the lumen of the tube.

11. The method of claim 1, wherein the distal end of the applicator comprises a resilient tip.

12. The method of claim 11, wherein the resilient tip comprises at least one material selected from the group consisting of plastic, polymer, rubber, cotton, gauze, and textiles.

13. The method of claim 1, wherein the distal end of the applicator has a rounded shape.

14. The method of claim 1, wherein the distal end of the applicator has a transverse end dimension that is larger than a transverse body dimension of an elongated body of the applicator.

15. The method of claim 1, wherein the tube comprises a first end located adjacent to the surgical site and a second end located further from the surgical site, and wherein the lumen of the tube has an inner maximum transverse dimension of 10 millimeters (mm) at the first end.

16. The method of claim 1, further comprising sterilizing the membrane.

17. A method for placing a membrane over a microfracture surgical site, the steps of the method comprising:
    disposing the membrane in a recess of a platform;
    coupling the platform to a tube;
    pushing the membrane coated with an active agent through a lumen of the tube and to the microfracture surgical site using an applicator; and
    positioning the membrane over at least a portion of the microfracture surgical site.

18. The method of claim 17, wherein the membrane comprises at least one selected from the group consisting of an amniotic membrane, human dermal grafts, animal dermal grafts, and therapeutic synthetic membranes.

19. The method of claim 17, wherein the active agent is selected from a group consisting of a medication, a growth factor, an anticoagulant, or a protein.

* * * * *